(12) United States Patent
Yu et al.

(10) Patent No.: US 6,808,716 B2
(45) Date of Patent: Oct. 26, 2004

(54) N-ACETYLAMINO ACIDS, RELATED N-ACETYL COMPOUNDS AND THEIR TOPICAL USE

(76) Inventors: Ruey J. Yu, 4 Lindenwold Ave., Ambler, PA (US) 19002; Eugene J. Van Scott, 3 Hidden La., Abington, PA (US) 19001

( * ) Notice: Subject to any disclaimer, the term of this patent is extended or adjusted under 35 U.S.C. 154(b) by 55 days.

(21) Appl. No.: 10/371,504

(22) Filed: Feb. 21, 2003

(65) Prior Publication Data

US 2003/0198656 A1 Oct. 23, 2003

Related U.S. Application Data

(63) Continuation-in-part of application No. 09/560,901, filed on Apr. 28, 2000, now Pat. No. 6,524,593, which is a continuation of application No. 09/227,213, filed on Jan. 8, 1999, now Pat. No. 6,159,485.

(51) Int. Cl.$^7$ .................................................. A61K 7/00
(52) U.S. Cl. ..................... 424/401; 514/2; 514/554; 514/557; 514/574; 514/844; 514/847
(58) Field of Search ........................... 424/401; 514/2, 514/554, 557, 574, 844, 847

(56) References Cited

U.S. PATENT DOCUMENTS

| | | |
|---|---|---|
| 3,932,622 A | 1/1976 | Friedman et al. |
| 4,603,146 A | 7/1986 | Kligman |
| 5,091,171 A | 2/1992 | Yu et al. |
| 5,112,613 A | 5/1992 | Honda et al. |
| 5,258,391 A | 11/1993 | Van Scott et al. |
| 5,378,455 A | 1/1995 | Kealey et al. |
| 5,385,938 A | 1/1995 | Yu et al. |
| 5,422,370 A | 6/1995 | Yu et al. |
| 5,451,405 A | 9/1995 | Zhang et al. |
| 5,468,476 A | 11/1995 | Ahluwalia et al. |
| 5,470,880 A | 11/1995 | Yu et al. |
| 5,472,698 A | 12/1995 | Rawlings et al. |
| 5,525,336 A | 6/1996 | Green et al. |
| 5,547,988 A | 8/1996 | Yu et al. |
| 5,641,475 A | 6/1997 | Yu et al. |
| 5,643,949 A | 7/1997 | Van Scott et al. |
| 5,652,273 A | 7/1997 | Henry et al. |
| 5,665,776 A | 9/1997 | Yu et al. |
| 5,733,535 A | 3/1998 | Hollingshead et al. |
| 6,159,485 A * | 12/2000 | Yu et al. ..................... 424/401 |
| 6,524,593 B1 * | 2/2003 | Yu et al. ..................... 424/401 |

FOREIGN PATENT DOCUMENTS

| | | |
|---|---|---|
| DE | 34 35 842 A1 | 4/1986 |
| EP | 0 328 099 A1 | 8/1989 |
| EP | 0 440 298 A1 | 8/1991 |
| FR | 2 244 541 A | 4/1975 |
| JP | 56-079618 A | 6/1981 |
| JP | 56-155298 A | 12/1981 |
| JP | 61-210013 A | 9/1986 |
| JP | 09-323915 A | 12/1997 |
| WO | WO 97/15283 A1 | 5/1997 |

OTHER PUBLICATIONS

Kligman, et al., "Topical tretinoin for photoaged skin," *Supplement to the Journal of American Academy of Dermatology*, vol. 15, No. 4, part 2, pp. 836–859 (Oct. 1986).

* cited by examiner

*Primary Examiner*—Thurman K. Page
(74) *Attorney, Agent, or Firm*—Akin Gump Strauss Hauer & Feld, L.L.P.

(57) ABSTRACT

Compositions comprising N-acetylamino acids and/or related N-acetyl compounds are useful to alleviate or improve various cosmetic conditions and dermatological disorders, including changes or damage to skin, nail and hair associated with intrinsic aging and/or extrinsic aging, as well as changes or damage caused by extrinsic factors. The N-acetylamino acid and/or related N-acetyl compound composition may further comprise a cosmetic, pharmaceutical or other topical agent to enhance or create synergetic effects.

20 Claims, No Drawings

N-ACETYLAMINO ACIDS, RELATED N-ACETYL COMPOUNDS AND THEIR TOPICAL USE

CROSS-REFERENCE TO RELATED APPLICATIONS

This application is a continuation-in-part of U.S. patent application Ser. No. 09/560,901, filed Apr. 28, 2000, now U.S. Pat. No. 6,524,593, issued Feb. 25, 2003, which itself is a continuation of U.S. patent application Ser. No. 09/227,213, filed Jan. 8, 1999, now U.S. Pat. No. 6,159,485 issued Dec. 12, 2000, the disclosures of which are incorporated herein by reference.

BACKGROUND OF THE INVENTION

This application relates to topical compositions containing additional N-acetylamino acids and related N-acetyl compounds, and their use in alleviating or improving various cosmetic conditions and dermatological disorders.

In PCT Application No. PCT/US96/16534, filed Oct. 16, 1996, entitled "Topical Compositions Containing N-Acetylcysteine and Odor Masking Materials," topical compositions comprising from 0.01% to 50% of N-acetylcysteine or a derivative of N-acetylcysteine, from 0.01% to 0.5% of an odor masking material, and a topical carrier are disclosed to improve the appearance of skin.

N-Acetylcysteine is N-acetylated cysteine which is a thiol containing amino acid, also called α-acetamido-β-mercaptopropanoic acid. Topical compositions containing N-acetylcysteine have been claimed to improve physical appearance of the skin including cosmetic wrinkles. N-acetylcysteine contains a free thiol group, thus, is known as an antioxidant. The affect of N-acetylcysteine is claimed to be due to its antioxidant property. N-Acetylcysteine, as an antioxidant substance, also has been indicated as protective against pulmonary oxygen toxicity (*Eur. Respir. J.* 2: 116-126 (1989)).

N-acetylcysteine, however, is also associated with a number of significant drawbacks. N-acetylcysteine is known to degrade under ordinary storage conditions and result in a malodorous smell. The malodor is suggested to be caused by the release of thiol compounds and hydrogen sulfide upon degradation. Thus, topical compositions containing N-acetylcysteine have little or no commercial use due to the strong malodor of N-acetylcysteine.

PCT/US96/16534 claimed that the malodor could be masked by addition of certain perfume chemicals at concentrations ranging from 0.01 to 0.5% by weight. The perfume chemicals include aromatic esters, aliphatic esters, aromatic alcohol, aliphatic alcohols, aliphatic ketones, aromatic aldehydes, aliphatic aldehydes, aromatic ethers and aliphatic ethers. Because the malodorous thiol compounds and hydrogen sulfide have not been chemically neutralized or destroyed, however, the transient masking effect is not a satisfactory solution for most consumers, and therefore is not a viable approach for commercialization of N-acetylcysteine in the cosmetic industry.

Our U.S. Pat. Nos. 6,159,485 and 6,524,593 disclose and claim N-acetyl aldosamines, N-acetylated amino acids and related compounds which are topically effective for various cosmetic conditions and dermatological indications including the signs of skin, nail and hair changes associated with intrinsic and/or extrinsic aging. The N-acetylated amino acids and related compounds do not necessarily contain thiol groups and are not necessarily antioxidants.

BRIEF SUMMARY OF THE INVENTION

It is an object of this invention to provide additional methods and compositions which can alleviate various cosmetic conditions and dermatological disorders including the signs of skin, nail and hair changes associated with intrinsic and/or extrinsic aging and extrinsic factors, and other skin conditions associated with or due to itching and/or inflammation, including pruritus.

We have now discovered additional N-acetylamino acids and related N-acetyl compounds which have unexpected properties. Topical applications of compositions comprising N-acetylamino acids and related N-acetyl compounds have been found to improve cosmetic conditions and dermatological disorders including cosmetic as well as clinical signs of changes in skin, nails and hair associated with intrinsic and/or extrinsic aging, or the damages caused by extrinsic factors such as sunlight, radiation, air pollution, wind, cold, dampness, heat, chemicals, smoke, cigarette smoking, and various oxidants.

The signs of skin changes associated with intrinsic and/or extrinsic aging and the skin damages caused by extrinsic factors include thinning of skin; fragile skin; deepening of skin lines and fine lines; wrinkles, including fine and course wrinkles; blemishes; atrophy; pigmented spots, blotches and mottles, nodules and mottled skin; pre-cancerous lesions; elastotic changes characterized by leathery, lusterless, uneven, coarse, rough, dry and/or yellowish skin; loss of skin elasticity and recoilability; loss of skin lubricating substances; changes in qualities and quantities of glycosaminoglycans and proteoglycans and collagen and elastic fibers; solar elastosis; decrease in collagen fibers; diminution in the number and diameter of elasitic fibers in the papillary dermis; atrophy; stretch marks; reduction in subcutaneous adipose tissue; deposition of abnormal elastic materials in the dermis leading to thickening of the dermis; older-looking skin; and telangiectatic skin.

The signs of nails and hair changes associated with intrinsic aging and the damages caused by extrinsic factors include thinning, fragility, splitting, lack of luster, uneven surface, and loss of flexibility and elasticity.

In accordance with the objects of the invention, compositions comprising at least one compound selected from the group consisting of certain N-acetylamino acids and related N-acetyl compounds, present in a therapeutically effective amount and in a pharmaceutically acceptable vehicle for topical treatment of cosmetic conditions or dermatological disorders are provided. In one embodiment of the invention, the compositions further comprise a cosmetic, pharmaceutical, or other topical agent.

Also in accordance with the objects of the invention, a method for treating cosmetic conditions and dermatological disorders comprising topically applying a therapeutically effective amount of a composition comprising at least one compound selected from the group consisting of certain N-acetylamino acids and related N-acetyl compounds, in a pharmaceutically acceptable vehicle is provided. In one embodiment of the invention, the method comprises topically applying a therapeutically effective amount of a composition comprising at least one compound selected from the group consisting of certain N-acetylamino acids and related N-acetyl compounds, and at least one cosmetic, pharmaceutical, or other topical agent, in a pharmaceutically acceptable vehicle.

The additional N-acetylamino acids and related N-acetyl compounds which are useful for topical treatment of skin, nail and hair changes associated with intrinsic and/or extrinsic aging and extrinsic factors include, inter alia, N-acetylamino acids selected from N-acetyl pyroglutamic acid, N-acetyl-phenylalaninol, N,S-diacetylamino acids, and isomeric or nonisomeric, free acid, salt, lactone, amide, or ester forms thereof; and related N-acetyl compounds selected from N-acetylpolyamines, N,N'-diacetylpolyamines, N-acetyl-caldine, N-acetyl-spermidine, N-acetyl-homospermidine, N-acetyl-thermine, N-acetyl-spermine, N-acetyl-thermospermine, N-acetyl-homospermine, N-acetyl-caldopentamine, N-acetyl-homocaldopentamine, N-acetyl-caldohexamine, N-acetyl-homocaldohexamine, N-acetyl-tris(3-aminopropyl)amine, N-acetyl-tetrakis(3-aminopropyl)amine, N-acetyl-amantadine, N-acetyl-adenosine, N-acetyl-adenosine-phosphoric acid, N-acetyl-piperazine, and N-acetyl guanine.

Additional objects and advantages of the invention will be set forth in part in the description that follows, and in part will be obvious from the description, or may be learned by practice of the invention. The objects and the advantages of this invention may be realized and obtained by means of the compositions and methods particularly pointed out in the appended claims.

DETAILED DESCRIPTION OF THE INVENTION

1. N-Acetylamino Acids and Related N-Acetyl Compounds (i) N-Acetylamino Acids

One aspect of the invention pertains to compositions comprising N-acetylamino acids, selected from N-acetyl-pyroglutamic acid, N-acetyl-phenylalaninol, and N,S-diacetylamino acids. The N-acetylamino acids may be present as isomeric or non-isomeric forms, as a free acid, salt, lactone, amide or ester form.

The N,S-diacetylamino acids and their esters, amides and salts include, for example, N,S-diacetyl-cysteine, N,S-diacetylhomocysteine, N,S-diacetyl-cysteine alkyl esters, and N,S-diacetylhomocysteine alkyl esters, particularly the methyl, ethyl, and propyl esters. The N,S-diacetylamino acids have been found to have antioxidant properties and to improve aging skin and dry skin.

(ii) Related N-Acetyl Compounds

Another aspect of the invention pertains to compositions comprising related or miscellaneous N-acetyl compounds. These N-acetyl compounds which are topically beneficial for various cosmetic and dermatologic indications include the following: N-acetyl and N,N'-diacetyl-1,3-diaminopropane, N-acetyl and N,N'-diacetyl-1,4-diaminobutane, N-acetyl and N,N'-diacetyl-1,5-diaminopentane, N-acetyl-caldine (also called N-acetyl-norspermidine; including mono, di and tri-N-acetyl caldine), N-acetyl-spermidine (including mono, di and tri-N-acetyl-spermidine), N-acetyl-homospermidine (including mono, di and tri-N-acetyl-homospermidine), N-acetyl-thermine (also called N-acetyl-norspermine; including mono, di, tri and tetra-N-acetyl-thermine), N-acetyl-spermine (including mono, di, tri and tetra-N-acetyl-spermine), N-acetyl-thermospermine (including mono, di, tri and tetra-N-acetyl-thermospermine), N-acetyl-homospermine (including mono, di, tri and tetra-N-acetyl-homospermine), N-acetyl-caldopentamine (including mono, di, tri, tetra and penta-N-acetyl-caldopentamine), N-acetyl-homocaldopentamine (including mono, di, tri, tetra and penta-N-acetyl-homocaldopentamine), N-acetyl-caldohexamine (including mono, di, tri, tetra, penta and hexa-N-acetyl-caldohexamine), N-acetyl-homocaldohexamine (including mono, di, tri, tetra, penta and hexa-N-acetyl-homocaldohexamine), N-acetyl-tris (3-aminopropyl)amine N-acetyl-tetrakis (3-aminopropyl)amine, N-acetyl-amantadine, N-acetyl-adenosine, N-acetyl-adenosine-phosphoric acid, N-acetyl-piperazine, and N-acetyl-guanine.

2. Topical Uses of N-Acetylamino Acids and Related N-Acetyl Compounds (i) N-Acetylamino Acids and Related N-Acetyl Compounds Compositions comprising the N-acetylamino acids or related N-acetyl compounds described herein are topically beneficial for various cosmetic conditions and dermatologic disorders, including those associated with intrinsic and/or extrinsic aging, as well as with changes or damage caused by extrinsic factors. These compositions can comprise one or more than one N-acetylamino acid or related N-acetyl compound. In a preferred embodiment, the compositions may be used for skin, hair and nail changes associated with intrinsic and/or extrinsic aging, and changes or damage caused by extrinsic factors.

With respect to age associated skin changes, the underlying bases of these changes is described in U.S. Pat. No. 4,603,146 (Kligman). In particular, the underlying causes of skin changes associated with aging can be more easily understood in view of the following summary of the changes in the epidermis and dermis as aging progresses.

With increasing age and exposure of a human to sun and other environmental traumas, cells divide at a slower rate (decreased capacity to renew themselves). They show marked irregularities in size, shape and staining properties; orderliness (polarity) from below to above is lost. The thickness of the epidermis decreases (atrophy). The horny layer which comprises the barrier against water loss and penetration of chemicals becomes abnormal due to the shedding (exfoliation) of cells in large group or clusters instead of as individual cells, resulting in roughness, scaling and dryness. There is loss of the orderly transformation of living epithelial cells into cornified dead cells which are shed at the surface, that is, differentiation is impaired. Aberrant differentiation results in numerous foci of abnormal epithelial growths or tumors, the most frequent and important of which are actinic keratoses. After many years these can transform into frank skin cancers called basal cell and squamous cell cancers. Pigment producing cells (melanocytes) can also become altered forming flat, dark growths (lentigo melanoma) which may progress to malignant melanoms.

The cells which make the fibers of the dermis become smaller and sparser with increasing age, usually in sun-damaged facial skin. There is a great loss of collagen fibers resulting in looseness and easy stretchability of the skin; elastic fibers become abnormal so that the skin does not promptly snap back after being stretched. Since the fibrous components comprise more than 90% of the bulk of skin of which 95% is collagen, the degradation of these fibers, especially collagen, is mainly responsible for wrinkling, laxness and loss of elasticity.

Additionally, small blood vessels become thin walled, dilated and often ruptured. Vascular supply thereby becomes compromised.

The signs of nail and hair changes associated with intrinsic aging and the damages caused by extrinsic factors include thinning of hair and nail plate; lack of lubricants and luster, and uneven surface of hair and nails; fragility and splitting of hair and nails; and reduction of flexibility, resiliency, and elasticity of hair and nails.

The conventional management of signs of aging skin has been the use of cosmetics, as well as medical procedures such as phenol, trichloroacetic acid, and other chemical peels, and plastic surgery, etc. Such medical procedures are costly and risky with serious side effects, and the treatments alter only the cosmetic appearance of the skin, without any significant modifications of the underlying aging process.

Topical application to the skin, hair or nails of a composition of the present invention is beneficial for various cosmetic conditions and dermatologic disorders including those associated with intrinsic and/or extrinsic aging and extrinsic factors, and also including those characterized by the foregoing changes to the skin, hair and nails. Exemplary indications are characterized as disturbed keratinization, defective syntheses of dermal components, and changes associated with aging of skin, nail and hair; and those indications which include dryness or loose of skin, nail and hair; xerosis; ichthyosis; palmar and plantar hyperkeratoses; uneven and rough surface of skin, nail and hair; dandruff; Darier's disease; lichen simplex chronicus; keratoses; acne; pseudofolliculitis barbae; eczema; psoriasis; itchy scalp and skin; pruritus; warts; herpes; age spots; lentigines; melasmas; blemished skin; hyperkeratoses; hyperpigmented skin; abnormal or diminished syntheses of collagen, glycosaminoglycans, proteoglycans and elastin as well as diminished levels of such components in the dermis; stretch marks; skin lines; fine lines; wrinkles; thinning of skin, nail plate and hair; skin thickening due to elastosis of photoaging, loss or reduction of skin, nail and hair resiliency, elasticity and recoilability; lack of skin, nail and hair lubricants and luster; dull and older-looking skin, nail and hair; fragility and splitting of nail and hair; and other topical conditions and indications.

(ii) Combination Compositions

In addition, compositions comprising one or more than one N-acetylamino acid or related N-acetyl compound of the invention may also be incorporated into a composition comprising a cosmetic, pharmaceutical or other topical agent to enhance or create synergetic effects.

In accordance with this aspect of the invention, the compositions of the present invention may contain one or more N-acetylamino acids and/or related N-acetyl compounds to magnify the therapeutic effect of an unrelated cosmetic or pharmaceutical agent. At least one compound selected from the group consisting of N-acetylamino acids and related N-acetyl compounds of the invention may be incorporated into composition containing a cosmetic or pharmaceutical agent for topical treatment to improve or alleviate signs of skin, nails or hair changes associated with intrinsic aging or the damages caused by extrinsic factors. It has been found that such incorporation results in magnified therapeutic efficacies which are not simply additive effects.

Most pharmaceutical drugs produce their therapeutic effects by first interacting with their receptors in the target tissues. Many drug receptors are functional macromolecules such as enzymes, cell membrane components or certain components of cells. The binding affinity or interacting property of a drug toward its specific receptor molecule is intimately governed by the chemical structure of the drug. Since most pharmaceutical agents are chemically different from N-acetyl compounds of the instant invention, the respective receptor molecule should be different and so are the pharmacological actions and the therapeutic effects. Under such conditions if an N-acetylamino acid and/or a related N-acetyl compound is incorporated into a composition containing a pharmaceutical agent, one of the following two consequences may arise:

(a) No enhancement or any substantial changes in either effect. In this case, the overall clinical effect would be a mixed effect, i.e. the effect due to the pharmaceutical agent alone mixed with the effect due to an N-acetylamino acid or related N-acetyl compound alone. Also in this case, the interaction between the pharmaceutical agent and its receptor molecule is not affected nor interfered by the presence of an N-acetylamino acid or related N-acetyl compound. Nor does the N-acetylamino acid or related N-acetyl compound assist in or enhance the binding affinity or the interaction of the pharmaceutical agent toward its receptor molecule. The clinical results from such combination composition would be just the mixed effects.

(b) Amplified therapeutic action or substantial loss of therapeutic action in either effect. In this case, the interaction between the pharmaceutical agent and its receptor molecule is affected either positively or negatively by the presence of an N-acetylamino acid or related N-acetyl compound. From the point of positive effect, an N-acetylamino acid or the related N-acetyl compound may produce an amplified effect by either increasing the affinity of the receptor molecule toward the pharmaceutical agent; acting as a better and more efficient coenzyme or as an activator by disrupting barriers and removing obstacles for better binding of the agent toward its receptor molecule; for example, enzyme activation by removal of natural inhibitors. In all these cases the overall clinical results would be due to magnified therapeutic effects which are not predictable from either effect alone.

From the point of negative effect, an N-acetylamino acid or related N-acetyl compound might interfere with or decrease the binding affinity of the pharmaceutical agent toward its receptor molecule; i.e. acting as an competitor or inhibitor. In such case, the overall clinical results should be due to substantial diminishment or complete loss of therapeutic effects, which is also unpredictable from either effect alone.

We have found that, in most cases, therapeutic effects of cosmetic and pharmaceutical agents are amplified when an N-acetylamino acid or related N-acetyl compound is incorporated into the composition, i.e., consequence (b) above is observed.

The cosmetic and pharmaceutical agents which may be actuated by an N-acetylamino acid or a related N-acetyl compound include those that improve or eradicate age spots, keratoses and wrinkles; local analgesics and anesthetics; antiacne agents; antibacterials; antiyeast agents; antifungal agents; antiviral agents; antidandruff agents; antidermatitis agents; antihistamine agents; antipruritic agents; antiemetics; antimotion sickness agents; antiinflammatory agents; antihyperkeratolytic agents; antiperspirants; antipsoriatic agents; antiseborrheic agents; hair conditioners and hair treatment agents; antiaging and antiwrinkle agents; sunblock and sunscreen agents; skin lightening agents; depigmenting agents; vitamins; corticosteroids; tanning agents; hormones; retinoids; and other dermatologicals.

Some examples of cosmetic and pharmaceutical agents are clotrimazole, ketoconazole, miconazole, griseoflivin, econazole, metronidazole, hydroxyzine, diphenhydramine, pramoxine, lidocaine, procaine, mepivacaine, monobenzone, erythromycin, tetracycline, clindamycin, meclocycline, hydroquinone, hydroquinone monoether, minocycline, naproxen, ibuprofen, theophylline, cromolyn, albuterol, retinol, retinyl acetate, retinyl palmitate, retinal, retinoic acid, 13-cis retinoic acid, hydrocortisone, hydrocortisone 21-acetate, hydrocortisone 17-valerate, hydrocortisone 17-butyrate, betamethasone valerate, betamethasone dipropionate, triamcinolone acetonide, fluocinonide, clobetasol, propionate, benzoyl peroxide, kojic acid, crotamiton, propranolol, promethazine, salicylic acid, vitamin E and vitamin E acetate.

Another example of cosmetic or other agents that may be combined with one or more N-acetyamino acids or related N-acetyl compounds of the invention include hydroxyacids, ketoacids and related compounds. Examples of hydroxy acids include hydroxymonocarboxylic acids, hydroxydicarboxylic acids, 2-hydroxycarboxylic acids, other hydroxycarboxylic, 2-ketocarboxylic acids acids and related compounds. See, for example, U.S. Pat. Nos. 5,422,370, 5,547,988, 5,470,880, and 5,385,938. The hydroxy acids may exist as a free acid, an ester, a lactone, in salt form with an organic base or an inorganic alkali, and as stereoisomers. Representative examples of hydroxy acids and related compounds include glycolic acid, mandelic acid, lactic acid, tropic acid, methyllactic acid, lactobionic acid, tartaric acid, citric acid, glucuronic acid, ribonic acid, gluconolactone, ribonolactone, gycolyl glycollate, lactyl lactate, trilactic acid and polylactic acid.

Yet another example of cosmetic or other agents that may be combined with one or more N-acetylamino acids or related N-acetyl compounds of the invention include phenyl alpha acyloxyalkanoic acids and derivatives thereof. These compounds may exist in a free acid, lactone or salt form, or as stereoisomers. See, for example, U.S. Pat. Nos. 5,258,391 and 5,643,949. Representative example of such compounds include diphenyl alpha acetoxyacetic acid, phenyl alpha acetoxyacetic acid, phenyl alpha methyl alpha acetoxyacetic acid, phenyl alpha acetoxypropanoic acid, and 2-phenyl beta acetoxypropanoic acid.

Still further, an N-acetylamino acid or related N-acetyl compound of the invention may be combined with one or more of the N-acetyl aldosamines, N-acetylamino acids or related N-acetyl compounds described and claimed in our U.S. Pat. Nos. 6,159,485 and 6,524,593.

3. General Preparation of the Cosmetic and Therapeutic Compositions

Compositions comprising N-acetylamino acids and/or related N-acetyl compounds of the instant invention may be formulated as solution, gel, lotion, cream, ointment, shampoo, spray, stick, powder, masque or other form topically acceptable for use on skin, nail and hair.

To prepare a solution composition, at least one N-acetyl compound of the instant invention is dissolved in a solution prepared from water, ethanol, propylene glycol, butylene glycol, diisopropyl adipate and/or other topically acceptable vehicle. The concentration of a single N-acetyl compound or the total concentration of all N-acetyl compounds, where the composition comprises more than one N-acetyl compound, may range from 0.01 to 99.9% by weight of the total composition, with preferred concentration of from 0.1 to 50% by weight of the total composition and with more preferred concentration of from 0.5 to 25% by weight of the total composition. Contemplated embodiments of the instant invention include ranges of 0.1% to 0.2%, 0.2% to 0.3%, 0.3% to 0.4%, 0.4% to 0.5%, 0.5% to 0.6%, 0.6% to 0.7%, 0.7% to 0.8%, 0.8% to 0.9%, 0.9% to 1%, 1% to 2%, 2% to 3%, 3% to 4%, 4% to 5%, 5% to 6%, 6% to 7%, 7% to 8%, 8% to 9%, 9% to 10%, 10% to 14%, 14% to 18%, 18% to 22%, 22% to 26%, 26% to 30%, 30% to 35%, 35% to 40%, 40% to 45%, 45% to 50%, 50% to 60%, 60% to 70%, 70% to 80%, 80% n to 90%, and 90% to 99.9% by weight of the total composition.

To prepare a topical composition in lotion, cream or ointment form, the N-acetyl compound is first dissolved in water, ethanol, propylene glycol, diisopropyl adipate and/or another vehicle, and the solution thus obtained is mixed with a desired base or pharmaceutically acceptable vehicle to make lotion, cream or ointment. Concentrations of the N-acetyl compound are the same as described above for the solution form.

A topical composition of the instant invention may also be formulated in a gel or shampoo form. A typical gel composition is formulated by the addition of a gelling agent such as chitosan, methyl cellulose, ethyl cellulose, polyvinyl alcohol, polyquaterniums, hydroxyethylcellulose, hydroxypropylcellulose, hydroxypropylmethylcellulose, carbomer or ammoniated glycyrrhizinate to a solution comprising the N-acetyl compound. The preferred concentration of the gelling agent may range from 0.1 to 4 percent by weight of the total composition. In the preparation of shampoo, the N-acetyl compound is first dissolved in water or propylene glycol, and the solution thus obtained is mixed with a shampoo base. Concentrations of the N-acetyl compound used in gel or shampoo form are the same as described above.

To prepare a combination composition for synergetic effects, a cosmetic, pharmaceutical or other topical agent is incorporated into any one of the above compositions by dissolving or mixing the agent into the formulation.

Other forms of compositions for topical delivery of N-acetyl compound of the instant invention are readily prepared or formulated by those skilled in the art.

The following are illustrative examples of formulations according to this invention. Although the examples utilize only selected compounds and formulations, it should be understood that the following examples are illustrative and not limiting. Therefore, any of the aforementioned N-acetyl compounds may be substituted according to the teachings of this invention in the following examples.

EXAMPLE 1

N-acetyl-1,3-diaminopropane (mixture of mono and diacetyl) 3 grams was dissolved in warm water 6 ml and propylene glycol 2 ml. The solution thus obtained was mixed with hydrophilic ointment 49 grams. The cream thus formulated had pH 4.8 and contained 5% N-acetylpolyamine.

EXAMPLE 2

N-acetyl-1,4-diamine (mixture of mono and diacetyl) 3 grams was dissolved in warm water 9 ml and propylene glycol 3 ml. The solution thus obtained was mixed with hydrophilic ointment 45 grams. The cream thus formulated had pH 5.1 and contained 5% N-acetylpolyamine.

EXAMPLE 3

N-acetyl-spermidine (mixture of mono, di and triacetyl) 2.5 grams was dissolved in water 5 ml and propylene glycol 2.5 ml. The solution thus obtained was mixed with hydrophilic ointment 40 grams. The cream thus formulated had pH 4.5 and contained 5% N-acetyl-spermidine.

EXAMPLE 4

N-acetyl-spermine (mixture of mono, di, tri and tetraacetyl) 2.5 grams was dissolved in water 5 ml and propylene glycol 2 ml. The solution thus obtained was mixed with hydrophilic ointment 40.5 grams. The cream thus formulated had pH 4.7 and contained 5% N-acetyl-spermine.

EXAMPLE 5

N,S-diacetyl-L-cysteine methyl ester 3 grams was dissolved in 97 ml solution prepared from ethanol 70 parts and propylene glycol 30 parts by volume. A clear solution thus prepared had pH 7.9 and contained 3% N,S-diacetyl-L-cysteine methyl ester.

EXAMPLE 6

N-acetyl-pyroglutamic acid 1 gram was dissolved in water 2 ml and propylene glycol 1 ml. The solution thus obtained was mixed with hydrophilic ointment 6 grams. The cream thus formulated had pH 1.8 and contained 10% N-acetyl-pyroglutamic acid.

EXAMPLE 7

N-acetyl-L-phenylalaninol 2.5 grams was dissolved in warm ethanol 5 ml and propylene glycol 2 ml. The solution thus obtained was mixed with hydrophilic ointment 40.5 grams. The cream thus formulated had pH 4.6 and contained 5% N-acetyl-L-phenylaianinol.

EXAMPLE 8

N-acetyl-adenosine 3 grams was dissolved in warm water 10 ml and propylene glycol 10 ml. The solution thus obtained was mixed with hydrophilic ointment 37 grams. The cream thus formulated had pH 4.5 and contained 5% N-acetyl-adenosine.

EXAMPLE 9

N-acetyl-adenosine-5'-monophosphoric acid 3 grams was dissolved in water 10 ml and propylene glycol 6 ml. L-Arginine 2 grams was added to make an amphoteric solution. The solution thus obtained was mixed with hydrophilic ointment 39 grams. The cream thus formulated had pH 6.0 and contained 5% N-acetyl-adenosine-5'-monophosphoric acid.

EXAMPLE 10

N-acetyl-amantadine 2.5 grams was dissolved in warm ethanol 5 ml, water 3 ml and propylene glycol 5 ml. The solution thus obtained was mixed with hydrophilic ointment 34.5 grams. The cream thus formulated had pH 4.2 and contained 5% N-acetyl-amantadine.

EXAMPLE 11

N-acetyl-piperazine (mono-acetyl) 2.5 grams was dissolved in water 7 ml and propylene glycol 4 ml. The solution thus obtained was mixed with hydrophilic ointment 36.5 grams. The cream thus formulated had pH 9.0 and contained 5% N-acetyl-piperazine.

EXAMPLE 12

$N^2$-acetyl-guanine 0.3 gram was dissolved in water 3 ml. The solution thus obtained was mixed with hydrophilic ointment 6.7 grams. The cream thus formulated had pH 2.6 and contained 3% $N^2$-acetyl-guanine.

EXAMPLE 13

For age spots treatment, the following combination formulation was used. N,S-diacetyl-L-cysteine methyl ester 3 grams, mandelic acid 5 grams, N-acetylglucosamine 5 grams, N-acetylproline 5 grams, citric acid 2 grams, tartaric acid 2 grams, malic acid 1 gram and arginine 3 grams were dissolved in 74 ml solution prepared from water 40 parts, ethanol 40 parts and propylene glycol 20 parts by volume.

4. Application and Treatment Using N-Acetylamino Acids and Related N-Acetyl Compounds The N-acetylamino acids and related N-acetyl compositions of the present invention may be applied to any area of the skin, hair, or nails. Exemplary areas of application include the hands, arms, neck, legs, feet, trunk, hair shaft, nails, including the nail plate and nail cuticle, and on and around the face. Exemplary areas of facial application include the nose, forehead, and areas around the eyes. The compositions may be applied with or without occlusion. Any suitable occlusive device may be used. In addition, it is within the knowledge of the skilled artisan how best to apply such occlusive devices to achieve the desired result.

The compositions of the present invention may be applied to these areas with varying frequency and for varying duration. In this regard, the skilled artisan will appreciate how to alter the frequency and duration of application to achieve the desired effect. For example, the compositions of the instant invention can be applied at varying frequencies including on a daily basis, 1 or more times daily, or 1 or more times weekly. When being applied on a daily basis, the instant invention can be applied 1, 2, 3 or more times a day. When being applied on a weekly basis the instant invention can be applied 1, 2, 3, 4, 5, 6, 7, 8, 9, 10, 11, 12 or more times a week. The duration of treatment with the compositions of the instant invention can also vary. For example, the compositions may be applied for 1, 2, 3, 4, 5, 6 or more weeks; or for 1, 2, 3, 4, 5, 6 or more months. The duration of treatment may also be continuous. Again, the skilled artisan will appreciate the interaction between frequency and duration of use in order to achieve and/or maintain the desired effect.

In addition, the skilled artisan will appreciate how to vary concentrations of the instant invention in conjunction with the frequency and duration of use to achieve the desired effect. For example, a composition of higher concentration might be applied with less frequency or for a shorter duration. In contrast, a composition of a lower concentration might be applied more frequently or for a longer duration.

The following are illustrative examples of treatments (methods of use) of the N-acetyl compounds of the invention. Although the examples utilize only selected compounds and formulations, it should be understood that the examples are only illustrative and not limiting.

EXAMPLE 14

A male subject age 69, having itchy back, topically applied the 5% N-acetyl polyamine cream of Example 2 above to the skin of his back. A few minutes after the topical application, the itch disappeared completely and the skin remained free of itch for the following 12 hours.

EXAMPLE 15

A male subject age 78, having red and itchy skin on his left forearm, topically applied the 5% N-acetyl-spermidine cream of Example 3 above to the involved skin. A few minutes after the topical application, the itch disappeared and the erythema gradually subsided.

EXAMPLE 16

A male subject age 68, having itchy skin on his left shoulder, topically applied the 5% N-acetyl-spermine cream of Example 4 above to the involved skin. A few minutes after the topical application, the itch disappeared completely and the skin was free of itch for the next 12 hours.

EXAMPLE 17

Antioxidant screen tests showed that N,S-diacetyl-L-cysteine methyl ester (see Example 5 above) is an antioxidant substance, and is beneficial for topical application of skin changes associated with aging The above solution was also effective for topical treatment of severe dry skin.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A composition comprising (A) a pharmaceutically acceptable vehicle for topical treatment of cosmetic conditions or dermatological disorders and (B) a therapeutically effective amount of at least one compound selected from the group consisting of (1) an N-acetylamino acid selected from the group consisting of N-acetyl pyroglutaminc acid, N-acetyl phenylalaninol, N,S-diacetylarmino acids, and isomeric or nonisomeric, free acid, salt, lactone, amide, or ester forms thereof, and (2) an N-acetyl compound selected from the group consisting of N-acetylpolyamines, N,N'-diacetylpolyamines, N-acetyl-caldine, N-acetyl-spermidine, N-acetyl-homospermidine, N-acetyl-thermine, N-acetyl-spermine, N-acetyl-thermospermine, N-acetyl-homospermine, N-acetyl-caldopentamine, N-acetyl-homocaldopentamine, N-acetyl-caldohexamine, N-acetyl-homocaldohexamine, N-acetyl-tris(3-aminopropyl)amine, N-acetyl-tetrakis(3-aminopropyl)amine, N-acetyl-amantadine, N-acetyl-adenosine, N-acetyl-adenosine-phosphoric acid, N-acetyl-piperazine, and N-acetyl guanine.

2. The composition of claim 1, wherein said N,S-diacetylamino acid is selected from the group consisting of N,S-diacetyl-cysteine, N,S-diacetyl-cysteine alkyl esters, N,S-diacetylhomocysteine, and N,S-diacetylhomocysteine alkyl esters.

3. The composition of claim 1, wherein said cosmetic conditions and dermatological disorders are selected from the group consisting of disturbed keratinization, defective syntheses of dermal components, and changes associated with aging of skin, nail and hair, conditions and disorders which include dryness or loose of skin, nail and hair, xerosis, ichthyosis, palmar hyerperkeratoses, plantar hyperkeratoses, uneven and rough surfaces of skin, nail and hair, dandruff, Darier's disease, lichen simplex chronicus, keratoses, acne, pseudofolliculitis barbae, eczema, psoriasis, pruritus, warts, herpes, age spots, lentigines, melasmas, blemished skin, hyperkeratoses, hyperpigmented skin, abnormal or diminished syntheses of collagen, glycosaminoglycans, proteoglycans and elastin as well as diminished levels of such components in the dermis, stretch marks, skin lines, fine lines, wrinkles, thinning of skin, nail plate and hair, skin thickening due to elastosis of photoaging, loss or reduction of skin, nail and hair resiliency, elasticity and recoilability, lack of skin, nail and hair lubricants and luster, dull and older-looking skin, nails and hair, and fragility and splitting of nails and hair.

4. A composition comprising:
(A) a pharmaceutically acceptable vehicle for topical treatment of cosmetic conditions or dermatological disorders,
(B) a therapeutically effective amount of at least one compound selected from the group consisting of (1) an N-acetylamino acid selected from the group consisting of N-acetyl pyroglutaminc acid, N-acetyl phenylalaninol, N,S-diacetylamino acids, and isomeric or nonisomeric, free acid, salt, lactone, amide, or ester forms thereof, and (2) an N-acetyl compound selected from the group consisting of N-acetylpolyamines, N,N'-diacetylpolyamines, N-acetyl-caldine, N-acetyl-spermidine, N-acetyl-homospermidine, N-acetyl-thermine, N-acetyl-spermine, N-acetyl-thermospermine, N-acetyl-homospermine, N-acetyl-caldopentamine, N-acetyl-homocaldopentamine, N-acetyl-caldohexamine, N-acetyl-homocaldohexamine, N-acetyl-tris(3-aminopropyl)amine, N-acetyl-tetrakis(3-aminopropyl)amine, N-acetyl-amantadine, N-acetyl-adenosine, N-acetyl-adenosine-phosphoric acid, N-acetyl-piperazine, and N-acetyl guanine, and
(C) a cosmetic, pharmaceutical or other topical agent.

5. The composition of claim 4, wherein said N-acetyl polyamine is selected from the group consisting of N-acetyl and N,N'-diacetyl derivatives of 1,3-diaminopropane, 1,4-diamino butane and 1,5-diaminopentane.

6. The composition of claim 4 wherein said N,S-diacetylamino acid is selected from the group consisting of N,S-diacetyl-cysteine, N,S-diacetyl-cysteine alkyl esters, N,S-diacetylhomocysteine, and N,S-diacetylhomocysteine alkyl esters.

7. The composition of claim 4, wherein said cosmetic conditions and dermatological disorders are selected from the group consisting of disturbed keratinization, defective syntheses of dermal components, and changes associated with aging of skin, nail and hair, conditions and disorders which include dryness or loose of skin, nail and hair, xerosis, ichthyosis, palmar hyerperkeratoses, plantar hyperkeratoses, uneven and rough surfaces of skin, nail and hair, dandruff, Darier's disease, lichen simplex chronicus, keratoses, acne, pseudofolliculitis barbae, eczema, psoriasis, pruritus, warts, herpes, age spots, lentigines, melasmas, blemished skin, hyperkeratoses, hyperpigmented skin, abnormal or diminished syntheses of collagen, glycosaminoglycans, proteoglycans and elastin as well as diminished levels of such components in the dermis, stretch marks, skin lines, fine lines, wrinkles, thinning of skin, nail plate and hair, skin thickening due to elastosis of photoaging, loss or reduction of skin, nail and hair resiliency, elasticity and recoilability, lack of skin, nail and hair lubricants and luster, dull and older-looking skin, nails and hair, and fragility and splitting of nails and hair.

8. The composition of claim 4, wherein said cosmetic, pharmaceutical, or other topical agent is selected from the group consisting of agents that improve or eradicate age spots, keratoses and wrinkles, local analgesics and anesthetics, antiacne agents, antibacterials, antiyeast agents, antifungal agents, antiviral agents, antidandruff agents, antidermatitis agents, antihistamine agents, antipruritic agents, antiemetics, antimotion sickness agents, antiinflammatory agents, antihyperkeratolytic agents, antiperspirants, antipsoriatic agents, antiseborrheic agents, hair conditioners and hair treatment agents, antiaging and antiwrinkle agents, sunblock and sunscreen agents, skin lightening agents, depigmenting agents, vitamins, corticosteroids, tanning agents, hormones, retinoids, and topical cardiovascular agents.

9. The composition of claim 8, wherein said cosmetic, pharmaceutical, or other topical agent is selected from, the group consisting of clotrimazole, ketoconazole, miconazole, griseofulvin, econazole, metronidazole, hydroxyzine, diphenhydramine, pramoxine, lidocaine, procaine, mepivacaine, monobenzone, erythromycin, tetracycline, clindamycin, meclocycline, hydroquinone, hydroquinone monoether, minocycline, naproxen, ibuprofen, theophylline, cromolyn, albuterol, retinol, retinyl acetate, retinyl palmitate, retinoic acid, 13-cis retinoic acid, hydrocortisone, hydrocortisone 21-acetate, hydrocortisone 17-valerate, hydrocortisone 17-butyrate, betamethasone valerate, betamethasone dipropionate, triamcinolone acetonide, fluocinonide, clobetasol propionate, benzoyl peroxide, crotamiton, propranolol, promethazine, salicylic acid, vitamin E and vitamin E acetate.

10. A composition comprising (A) a pharmaceutically acceptable vehicle for topical treatment of cosmetic conditions or dermatological disorders and (B) at least 1% by total weight of the composition of at least one compound selected from the group consisting of (1) an N-acetyamino acid selected from the group consisting of N-acetyl pyroglutaminc acid, N-acetyl phenylalaninol, N,S-diacetylamino acids, and isomeric or nonisomeric, free acid, salt, lactone, amide, or ester forms thereof, and (2) an N-acetyl compound selected from the group consisting of N-acetylpolyamines, N,N'-diacetylpolyamines, N-acetyl-caldine, N-acetyl-spernidine, N-acetyl-homospermidine, N-acetyl-thermine, N-acetyl-spermine, N-acetyl-thermospermine, N-acetyl-homospermine, N-acetyl-caldopentamine, N-acetyl-homocaldopentamine, N-acetyl-caldohexamine, N-acetyl-homocaldohexamine, N-acetyl-tris(3-aminopropyl)amine, N-acetyl-tetrakis(3-aminopropyl)amine, N-acetyl-amantadine, N-acetyl-adenosine, N-acetyl-adenosine-phosphoric acid, N-acetyl-piperazine, and N-acetyl guanine.

11. A composition comprising:
(A) a pharmaceutically acceptable vehicle for topical treatment of cosmetic conditions or dermatological disorders,
(B) at least 1% by total weight of the composition of at least one compound selected from the group consisting of (1) an N-acetylamino acid selected from the group consisting of N-acetyl pyroglutaminc acid, N-acetyl phenylalaninol, N,S-diacetylamino acids, and isomeric or nonisomeric, free acid, salt, lactone, amide, or ester forms thereof, and (2) an N-acetyl compound selected from the group consisting of N-acetylpolyamines, N,N'-diacetylpolyamines, N-acetyl-caldine, N-acetyl-spermidine, N-acetyl-homospermidine, N-acetyl-thermine, N-acetyl-spermine, N-acetyl-thermospermine, N-acetyl-homospermine, N-acetyl-caldopentamine, N-acetyl-homocaldopentamine, N-acetyl-caldohexamine, N-acetyl-homocaldohexamine, N-acetyl-tris(3-aminopropyl) amine, N-acetyl-tetrakis(3-aminopropyl)amine, N-acetyl-amantadine, N-acetyl-adenosine, N-acetyl-adenosine-phosphoric acid, N-acetyl-piperazine, and N-acetyl guanine, and
(C) a cosmetic, pharmaceutical or other topical agent.

12. A method for treating cosmetic conditions and dermatological disorders comprising topically applying a composition comprising (A) a pharmaceutically acceptable vehicle for topical treatment of cosmetic conditions or dermatological disorders and (B) a therapeutically effective amount of a composition comprising at least one compound selected from the group consisting of (1) an N-acetylamino acid selected from the group consisting of N-acetyl pyroglutaminc acid, N-acetyl phenylalaninol, N,S-diacetylamino acids, and isomeric or nonisomeric, free acid, salt, lactone, amide, or ester forms thereof, and (2) an N-acetyl compound selected from the group consisting of N-acetylpolyamines, N,N'-diacetylpolyamines, N-acetyl-caldine, N-acetyl-spermidine, N-acetyl-homospermidine, N-acetyl-thermine, N-acetyl-spermine, N-acetyl-thermospermine, N-acetyl-homospermine, N-acetyl-caldopentamine, N-acetyl-homocaldopentamine, N-acetyl-caldohexamine, N-acetyl-homocaldohexamine, N-acetyl-tris(3-aminopropyl)amine, N-acetyl-tetrakis(3-aminopropyl)amine, N-acetyl-amantadine, N-acetyl-adenosine, N-acetyl-adenosine-phosphoric acid, N-acetyl-piperazine, and N-acetyl guanine.

13. The method of claim 12, wherein said N,S-diacetylamino acid is selected from the group consisting of N,S-diacetyl-cysteine, N,S-diacetyl-cysteine alkyl esters, N,S-diacetylhomocysteine, and N,S-diacetylhomocysteine alkyl esters.

14. The method of claim 12, wherein said cosmetic conditions and dermatological disorders are selected from the group consisting of disturbed keratinization, defective syntheses of dermal components, and changes associated with aging of skin, nail and hair, conditions and disorders which include dryness or loose of skin, nail and hair, xerosis, ichthyosis, palmar hyerperkeratoses, plantar hyperkeratoses, uneven and rough surfaces of skin, nail and hair, dandruff, Darier's disease, lichen simplex chronicus, keratoses, acne, pseudofolliculitis barbae, eczema, psoriasis, pruritus, warts, herpes, age spots, lentigines, melasmas, blemished skin, hyperkeratoses, hyperpigmented skin, abnormal or diminished syntheses of collagen, glycosaminoglycans, proteoglycans and elastin as well as diminished levels of such components in the dermis, stretch marks, skin lines, fine lines, wrinkles, thinning of skin, nail plate and hair, skin thickening due to elastosis of photoaging, loss or reduction of skin, nail and hair resiliency, elasticity and recoilability, lack of skin, nail and hair lubricants and luster, dull and older-looking skin, nails and hair, and fragility and splitting of nails and hair.

15. A method for treating cosmetic conditions and dermatological disorders comprising topically applying a composition comprising:
(A) a pharmaceutically acceptable vehicle for topical treatment of cosmetic conditions or dermatological disorders,
(B) a therapeutically effective amount of at least one compound selected from the group consisting of (1) an N-acetylamino acid selected from the group consisting of N-acetyl pyroglutaminc acid, N-acetyl phenylalaninol, N,S-diacetylamino acids, and isomeric or nonisomeric, free acid, salt, lactone, amide, or ester forms thereof, and (2) an N-acetyl compound selected from the group consisting of N-acetylpolyamines, N,N'-diacetylpolyamines, N-acetyl-caldine, N-acetyl-spermidine, N-acetyl-homospermidine, N-acetyl-thermine, N-acetyl-spermine, N-acetyl-thermospermine, N-acetyl-homospermine, N-acetyl-caldopentamine, N-acetyl-homocaldopentamine, N-acetyl-caldohexamine, N-acetyl-homocaldohexamine, N-acetyl-tris(3-aminopropyl) amine, N-acetyl-tetrakis(3-aminopropyl)amine, N-acetyl-amantadine, N-acetyl-adenosine, N-acetyl-adenosine-phosphoric acid, N-acetyl-piperazine, and N-acetyl guanine, and
(C) a cosmetic, pharmaceutical or other topical agent.

16. The method of claim 15, wherein said N-acetyl polyamine is selected from the group consisting of N-acetyl and N,N'-diacetyl derivatives of 1,3-diaminopropane, 1,4-diamino butane and 1,5-diaminopentane.

17. The method of claim 15, wherein said N,S-diacetylamino acid is selected from the group consisting of N,S-diacetyl-cysteine, N,S-diacetyl-cysteine alkyl esters, N,S-diacetylhomocysteine, and N,S-diacetylhomocysteine alkyl esters.

18. The method of claim 15, wherein said cosmetic conditions and dermatological disorders are selected from the groups consisting of disturbed keratinization, defective syntheses of dermal components, and changes associated with aging of skin, nail and hair, conditions and disorders which include dryness or loose of skin, nail and hair, xerosis, ichthyosis, palmar hyerperkeratoses, plantar hyperkeratoses, uneven and rough surfaces of skin, nail and hair, dandruff, Darier's disease, lichen simplex chronicus, keratoses, acne, pseudofolliculitis barbae, eczema, psoriasis, pruritus, warts, herpes, age spots, lentigines, melasmas, blemished skin, hyperkeratoses, hyperpigmented skin, abnormal or diminished syntheses of collagen, glycosaminoglycans, proteoglycans and elastin as well as diminished levels of such components in the dermis, stretch marks, skin lines, fine lines, wrinkles, thinning of skin, nail plate and hair, skin thickening due to elastosis of photoaging, loss or reduction of skin, nail and hair resiliency, elasticity and recoilability, lack of skin, nail and hair lubricants and luster, dull and older-looking skin, nails and hair, and fragility and splitting of nails and hair.

19. The method of claim 15, wherein said cosmetic, pharmaceutical, or other topical agent is selected from the group consisting of agents that improve or eradicate age spots, keratoses and wrinkles, local analgesics and anesthetics, antiacne agents, antibacterials, antiyeast agents, antifungal agents, antiviral agents, antidandruff agents, antidermatitis agents, antihistamine agents, antipruritic agents, antiemetics, antimotion sickness agents, antiinflammatory agents, antihyperkeratolytic agents, antiperspirants, antipsoriatic agents, antiseborrheic agents, hair conditioners and hair treatment agents, antiaging and antiwrinkle agents, sunblock and sunscreen agents, skin lightening agents, depigmenting agents, vitamins, corticosteroids, tanning agents, hormones, retinoids, and topical cardiovascular agents.

20. The method of claim 19, wherein said cosmetic, pharmaceutical, or other topical agent is selected from the group consisting of clotrimazole, ketoconazole, miconazole, griseofulvin, econazole, metronidazole, hydroxyzine, diphenhydramine, pramoxine, lidocaine, procaine, mepivacaine, monobenzone, erythromycin, tetracycline, clindamycin, meclocycline, hydroquinone, hydroquinone monoether, minocycline, naproxen, ibuprofen, theophylline, cromolyn, albuterol, retinol, retinyl acetate, retinyl palmitate, retinoic acid, 13-cis retinoic acid, hydrocortisone, hydrocortisone 21-acetate, hydrocortisone 17-valerate, hydrocortisone 17-butyrate, betamethasone valerate, betamethasone dipropionate, triamcinolone acetonide, fluocinonide, clobetasol propionate, benzoyl peroxide, crotamiton, propranolol, promethazine, salicylic acid, vitamin E, and vitamin E acetate.

* * * * *